United States Patent
Hosoya et al.

(10) Patent No.: US 8,030,266 B2
(45) Date of Patent: Oct. 4, 2011

(54) METHOD FOR PRODUCTION OF PEARLESCENT COMPOSITION COMPRISING A FATTY ACID GLYCOL ESTER MIXTURE

(75) Inventors: Shingo Hosoya, Wakayama (JP); Koji Mine, Wakayama (JP); Takeshi Nakai, Wakayama (JP)

(73) Assignee: KAO Corporation, Tokyo (JP)

( * ) Notice: Subject to any disclaimer, the term of this patent is extended or adjusted under 35 U.S.C. 154(b) by 0 days.

(21) Appl. No.: 12/595,415

(22) PCT Filed: Apr. 7, 2008

(86) PCT No.: PCT/JP2008/056848
§ 371 (c)(1),
(2), (4) Date: Oct. 9, 2009

(87) PCT Pub. No.: WO2008/126816
PCT Pub. Date: Oct. 23, 2008

(65) Prior Publication Data
US 2010/0105861 A1    Apr. 29, 2010

(30) Foreign Application Priority Data
Apr. 9, 2007 (JP) .................. 2007-101851

(51) Int. Cl.
*C11D 1/83* (2006.01)
*C11D 10/02* (2006.01)

(52) U.S. Cl. ........ 510/416; 510/421; 510/422; 510/426; 510/427; 510/437; 510/491

(58) Field of Classification Search .................. 510/416, 510/421, 422, 426, 427, 437, 491
See application file for complete search history.

(56) References Cited

U.S. PATENT DOCUMENTS

| | | | | |
|---|---|---|---|---|
| 4,777,038 A | * | 10/1988 | Scheuffgen | 424/70.31 |
| 6,165,955 A | * | 12/2000 | Chen et al. | 510/123 |
| 6,210,659 B1 | * | 4/2001 | Wilhelm et al. | 424/70.24 |
| 7,268,106 B2 | * | 9/2007 | Arai | 510/130 |
| 2007/0213243 A1 | * | 9/2007 | Yao et al. | 510/130 |
| 2008/0319090 A1 | * | 12/2008 | Frantz et al. | 514/772 |
| 2009/0088363 A1 | * | 4/2009 | Panandiker et al. | 510/343 |

FOREIGN PATENT DOCUMENTS

| | | |
|---|---|---|
| JP | 2-286612 A | 11/1990 |
| JP | 4-29913 A | 1/1992 |
| JP | 4-45843 A | 2/1992 |
| JP | 5-202386 A | 8/1993 |
| JP | 6-182173 A | 7/1994 |
| JP | 9-188614 A | 7/1997 |
| JP | 2001-302449 A | 10/2001 |
| JP | 2003-155214 A | 5/2003 |
| JP | 2004-277314 A | 10/2004 |

OTHER PUBLICATIONS

Office Action issued Mar. 28, 2011, in Chinese patent Application No. 200880011220.7 (with English translation).

* cited by examiner

*Primary Examiner* — Charles Boyer
(74) *Attorney, Agent, or Firm* — Birch, Stewart, Kolasch & Birch, LLP.

(57) ABSTRACT

A method for producing a pearly luster composition containing pearly luster particles (A) containing a fatty acid glycol ester (a1) and a fatty acid glycol ester (a2) having a melting point higher than the melting point of the fatty acid glycol ester (a1), and a surfactant (B), wherein the method includes the steps of (i) solubilizing the fatty acid glycol ester (a2) in the presence of the surfactant (B); (ii) mixing the solubilized solution obtained in the step (i) with a molten fatty acid glycol ester (a1), to emulsify the mixture; and (iii) cooling the emulsified mixture obtained in the step (ii), to precipitate the pearly luster particles (A); a pearly luster composition obtained by the method; and a shampoo containing the pearly luster composition. The pearly luster composition obtained by the present invention is suitably used for shampoos, conditioners, body shampoos, liquid detergents, and the like.

16 Claims, No Drawings

METHOD FOR PRODUCTION OF PEARLESCENT COMPOSITION COMPRISING A FATTY ACID GLYCOL ESTER MIXTURE

TECHNICAL FIELD

The present invention relates to a pearly luster composition, a method for producing the pearly luster composition, and a shampoo containing the pearly luster composition. More specifically, the present invention relates to a pearly luster composition, which can be suitably used to enhance the added values of shampoos, conditioners, body shampoos, liquid detergents, and the like, a method for producing the pearly luster composition, and a shampoo containing the pearly luster composition.

BACKGROUND ART

As pearly luster particles which are excellent in high-temperature stability, Patent Publication 1 describes a mildly cold pearly luster concentrate containing a pearly luster coloring agent which consists essentially of a fatty acid base material selected from the group consisting of hydroxyl stearate, polyethylene glycol mono- and di-stearates, ethylene glycol mono- and di-stearates, stearic acid monoethanolamide, and mixtures thereof, wherein at least about 90% by weight of the fatty acids of the above fatty acid base material is composed of octadecanoic acid. However, in order to obtain the pearly luster coloring agent, it is necessary to use a high-purity octadecanoic acid purified from fatty acid raw materials. Therefore, the cost involved in manufacturing increases.
Patent Publication 1: JP2001-514627 A

SUMMARY OF THE INVENTION

The present invention relates to:

[1] a method for producing a pearly luster composition containing pearly luster particles (A) containing a fatty acid glycol ester (a1) represented by the formula (I):

wherein each of $R^1$ and $R^2$ is independently an alkyl group having 13 to 21 carbon atoms, $A^1$ is a —$C_2H_4$— group or a —$C_3H_6$— group, and x is the number of from 1 to 10, and a fatty acid glycol ester (a2) represented by the formula (II):

wherein each of $R^3$ and $R^4$ is independently an alkyl group having 15 to 21 carbon atoms, $A^2$ is a —$C_2H_4$— group or a —$C_3H_6$— group, and y is the number of from 1 to 10, the fatty acid glycol ester having a melting point higher than the melting point of the fatty acid glycol ester (a1), and a surfactant (B),
wherein the method includes the steps of;
(i) solubilizing the fatty acid glycol ester (a2) in the presence of the surfactant (B);
(ii) mixing the solubilized solution obtained in the step (i) with a molten fatty acid glycol ester (a1), to emulsify the mixture; and
(iii) cooling the emulsified mixture obtained in the step (ii), to precipitate the pearly luster particles (A);
[2] a pearly luster composition obtained by the method as defined in the above [1]; and
[3] a shampoo containing the pearly luster composition as defined in the above [2].

DETAILED DESCRIPTION OF THE INVENTION

The present invention relates to a method that can produce at a low cost a pearly luster composition containing pearly luster particles which are excellent in luster while being stable even at a high temperature.

The present inventors have found that a fatty acid glycol ester having a high melting point is solubilized in the presence of a surfactant, and subsequently mixed with a fatty acid glycol ester having a melting point lower than the melting point of the above fatty acid glycol ester, and whereby pearly luster particles which are excellent in luster while being stable even at a high temperature are precipitated. The present invention has been accomplished thereby.

According to the present invention, the pearly luster composition containing pearly luster particles which are excellent in luster while being stable even at a high temperature can be produced at a low cost.

The present invention is a method for obtaining a composition for pearly luster containing pearly luster particles (A) containing a fatty acid glycol ester (a1) and a fatty acid glycol ester (a2), and a surfactant (B), using at least a fatty acid glycol ester (a1), a fatty acid glycol ester (a2), and a surfactant (B) as raw materials for pearly luster.

The fatty acid glycol ester (a1) is represented by the formula (I):

wherein each of $R^1$ and $R^2$ is independently an alkyl group having 13 to 21 carbon atoms, $A^1$ is a —$C_2H_4$— group or a —$C_3H_6$— group, and x is the number of from 1 to 10.

In the formula (I), each of $R^1$ and $R^2$ is independently an alkyl group having 13 to 21 carbon atoms. The number of carbon atoms of the alkyl group is from 13 to 21, and preferably from 15 to 21, from the viewpoint of exhibiting an excellent pearly luster.

In the formula (I), $A^1$ is a —$C_2H_4$— group or a —$C_3H_6$— group, and preferably a —$C_2H_4$— group. x is the number of from 1 to 10, preferably the number of from 1 to 5, and more preferably the number of from 1 to 3.

In addition, as the fatty acid glycol ester (a1), those having a melting point of 50° C. or higher and being crystalline are preferable.

Specific examples of the preferred fatty acid glycol ester (a1) include monoethylene glycols such as ethylene glycol distearate, ethylene glycol dimyristate, ethylene glycol dipalmitate, and ethylene glycol dibehenate; diethylene glycols such as diethylene glycol distearate, diethylene glycol dimyristate, diethylene glycol dipalmitate, and diethylene glycol dibehenate; and triethylene glycols such as triethylene glycol distearate, triethylene glycol dimyristate, triethylene glycol dipalmitate, and triethylene glycol dibehenate; and the like. These fatty acid glycol esters can be used alone or in admixture of two or more kinds. Here, when two or more kinds of the fatty acid glycol esters are used together, the fatty acid glycol ester may be a mixture of the fatty acid glycol esters each prepared, or may be a mixture of the fatty acid glycol esters obtained by a reaction using a mixture of fatty acids having different lengths of the alkyl chains and glycol. For example, from the reaction of a mixture of palmitic acid and stearic acid with glycol, a mixture of ethylene glycol dipalmitate, ethylene glycol monopalmitate and monostearate, and ethylene glycol distearate is obtained. Among them, the monoethylene glycols (fatty acid ethylene glycols) are preferable, and ethylene glycol distearate, ethylene glycol dimyristate, ethylene glycol dipalmitate, and ethylene glycol dibehenate, and a mixture of ethylene glycol dipalmitate, ethylene glycol monopalmitate and ethylene glycol monostearate, and ethylene glycol distearate are more preferable.

The fatty acid glycol ester (a1) is formulated in an amount of preferably 15% by weight or more, and more preferably 18% by weight or more, of the raw materials for pearly luster, from the viewpoint of exhibiting a sufficient pearly luster, and in an amount of preferably 30% by weight or less, and more preferably 25% by weight or less, of the raw materials for pearly luster, from the viewpoint of suppressing an increase in the viscosity of the pearly luster composition and increasing fluidity. From these viewpoints, the fatty acid glycol ester is formulated in an amount of preferably from 15 to 30% by weight, more preferably from 15 to 25% by weight, and even more preferably from 18 to 25% by weight, of the raw materials for pearly luster.

The fatty acid glycol ester (a2) is represented by the formula (II):

$$R^3COO\text{-}(A^2O)_y\text{—}COR^4 \qquad (II)$$

wherein each of $R^3$ and $R^4$ is independently an alkyl group having 15 to 21 carbon atoms, $A^2$ is a —$C_2H_4$— group or a —$C_3H_6$— group, and y is the number of from 1 to 10.

In the formula (II), each of $R^3$ and $R^4$ is independently an alkyl group having 15 to 21 carbon atoms. The number of carbon atoms of the alkyl group is from 15 to 21, and preferably from 17 to 21, from the viewpoint of exhibiting high-temperature stability.

In the formula (II), $A^2$ is a —$C_2H_4$— group or a —$C_3H_6$— group, and preferably a —$C_2H_4$— group. y is the number of from 1 to 10, preferably the number of from 1 to 5, and more preferably the number of from 1 to 3.

As the fatty acid glycol ester (a2), those having a melting point higher than the melting point of the fatty acid glycol ester (a1) are used. The fatty acid glycol ester (a2) has a melting point higher than the melting point of the fatty acid glycol ester (a1) preferably by 5° C. or more, and more preferably by 10° to 20° C., from the viewpoint of storage stability at a high temperature. Also, the fatty acid glycol ester (a2) has a melting point of preferably 60° C. or more, from the viewpoint of high-temperature stability.

In addition, as the fatty acid glycol ester (a2), those being crystalline are preferable.

Specific examples of the preferred fatty acid glycol ester (a2) include monoethylene glycols such as ethylene glycol distearate, ethylene glycol dimyristate, ethylene glycol dipalmitate, and ethylene glycol dibehenate; diethylene glycols such as diethylene glycol distearate, diethylene glycol dimyristate, diethylene glycol dipalmitate, and diethylene glycol dibehenate; and triethylene glycols such as triethylene glycol distearate, triethylene glycol dimyristate, triethylene glycol dipalmitate, and triethylene glycol dibehenate; and the like. These fatty acid glycol esters can be used alone or in admixture of two or more kinds. Among them, the monoethylene glycols (fatty acid ethylene glycols) are preferable, ethylene glycol distearate, ethylene glycol dimyristate, ethylene glycol dipalmitate, and ethylene glycol dibehenate, are more preferable, and ethylene glycol distearate is even more preferable.

The fatty acid glycol ester (a2) is formulated in an amount preferably less than the amount of the fatty acid glycol ester (a1) formulated, and in an amount of more preferably 1/100 or more and less than 1/2, and even more preferably 1/50 or more and 1/4 or less, of the amount of the fatty acid glycol ester (a1).

The surfactant is effective in promoting emulsification of the pearly luster composition, and an anionic surfactant and a nonionic surfactant are suitably used.

The anionic surfactant includes fatty acid salts, alkyl sulfates, polyoxyalkylene alkyl ether sulfates, sulfosuccinate surfactants, polyoxyalkylene alkylamido ether sulfates, monoglyceride sulfates, olefin sulfonates, alkyl benzene sulfonates, alkane sulfonates, acyl isethionates, acyl amino acids, alkyl phosphates, polyoxyalkylene alkyl ether phosphates, polyoxyalkylene alkyl ether carboxylates, and the like. Among them, alkyl sulfates are preferable.

Examples of the alkyl sulfates include alkyl sulfates which may have a polyoxyalkylene group represented by the formula (III):

$$R^5\text{—}O\text{—}(R^6O)_m\text{—}SO_3M \qquad (III)$$

wherein $R^5$ is a linear or branched, saturated or unsaturated hydrocarbon group having 8 to 20 carbon atoms, $R^6$ is an ethylene group or a propylene group, M is an alkali metal, an alkaline-earth metal, an ammonium ion, or a hydroxyalkyl-substituted ammonium having 2 or 3 carbon atoms, and m is the number of from 0 to 8, which means an average number of moles, and the like.

In the formula (III), $R^5$ is a linear or branched, saturated or unsaturated hydrocarbon group having 8 to 20 carbon atoms, and preferably an alkyl group having 8 to 20 carbon atoms or an alkenyl group having 8 to 20 carbon atoms. Preferred examples of $R^5$ include a lauryl group, a myristyl group, a palmityl group, a stearyl group, and the like.

$R^6$ is an ethylene group or a propylene group. Specific examples of $R^6$ include an ethylene group, an n-propylene group, and an iso-propylene group.

M is an alkali metal, an alkaline-earth metal, an ammonium ion, or a hydroxyalkyl-substituted ammonium having 2 or 3 carbon atoms, and preferably an alkali metal.

m is the number of from 0 to 8, and preferably the number of from 0 to 4.

Preferred examples of the alkyl sulfates include sodium lauryl sulfate, triethanolamine lauryl sulfate, sodium polyoxyethylene lauryl ether sulfate, triethanolamine polyoxyethylene lauryl ether sulfate, and the like. These alkyl sulfates can be used alone or in admixture of two or more kinds.

The anionic surfactant is formulated in an amount of preferably 5% by weight or more and more preferably 8% by weight or more, of the raw materials for pearly luster, from the viewpoint of homogeneously mixing each component, and the anionic surfactant is formulated in an amount of preferably 15% by weight or less and more preferably 13% by weight or less, of the raw materials for pearly luster, from the viewpoint of suppressing an increase in the viscosity of the pearly luster composition and increasing fluidity. From the above viewpoints, the anionic surfactant is formulated in an amount of preferably from 5 to 15% by weight, more preferably from 8 to 15% by weight, and even more preferably from 8 to 13% by weight, in the raw materials for pearly luster.

The nonionic surfactant includes those having a polyoxyalkylene group such as a polyoxyethylene group or a polyoxypropylene group.

The nonionic surfactant has an HLB value of preferably less than 15, and more preferably from 9 to 12, from the viewpoint of lowering the viscosity. Here, the HLB value is an index showing a hydrophilic-lipophilic balance. In the present invention, the HLB value is a value calculated using the equation according to Oda and Teramura, et al.:

HLB Value=(ΣInorganic Value/ΣOrganic Value)×10

Specific examples of the nonionic surfactant include polyoxyalkylene alkyl ethers, polyoxyalkylene alkylphenyl ethers, polyoxyalkylene glycol fatty acid esters, polyoxyalkylene fatty acid esters, polyoxyalkylene sorbitan fatty acid esters, polyoxyalkylene fatty acid monoalkanolamides, polyoxyalkylene fatty acid dialkanolamides, and the like. These polyoxyalkylene nonionic surfactants can be used alone or in admixture of two or more kinds. Among them, a polyoxyalkylene alkyl ether represented by the formula (IV):

$$R^7\text{—}O\text{—}(R^8O)_n\text{—}H \quad (IV)$$

wherein $R^7$ is a linear or branched, saturated or unsaturated hydrocarbon group having 8 to 20 carbon atoms, $R^8$ is an ethylene group or a propylene group, and n is the number of from 1 to 10, which means an average number of moles, is preferable, and polyoxyethylene lauryl ether is more preferable.

In the formula (IV), $R^7$ is a linear or branched, saturated or unsaturated hydrocarbon group having 8 to 20 carbon atoms, and preferably an alkyl group having 8 to 20 carbon atoms or an alkenyl group having 8 to 20 carbon atoms. Preferred examples of $R^5$ include a lauryl group, a myristyl group, a palmityl group, a stearyl group, and the like.

$R^8$ is an ethylene group or a propylene group. Specific examples of $R^8$ include an ethylene group, an n-propylene group, and an iso-propylene group.

n is the number of from 1 to 10, and preferably the number of from 3 to 7.

The nonionic surfactant is formulated in an amount of preferably 0.5% by weight or more and more preferably 1% by weight or more, of the raw materials for pearly luster, from the viewpoint of suppressing an increase in the viscosity of the pearly luster composition and increasing fluidity, and the nonionic surfactant is formulated in an amount of preferably 10% by weight or less, more preferably 8% by weight or less, and even more preferably 5% by weight or less, of the raw materials for pearly luster, from the viewpoint of exhibiting an excellent pearly texture. From the above viewpoints, the nonionic surfactant is formulated in an amount of preferably from 0.5 to 10% by weight, more preferably from 0.5 to 8% by weight, and even more preferably from 1 to 5% by weight, of the raw materials for pearly luster.

Incidentally, a fatty acid monoalkylolamide may be used as the raw materials for pearly luster, from the viewpoint of increasing luster.

Representative examples of the fatty acid monoalkylolamide include, for example, a fatty acid monoalkylolamide represented by the formula (V):

$$R^9CO\text{—}NH\text{—}R^{10}OH \quad (V)$$

wherein $R^9$ is a linear or branched, saturated or unsaturated hydrocarbon group having 7 to 20 carbon atoms, and $R^{10}$ is an ethylene group or a propylene group.

Specific examples of the preferred fatty acid monoalkylolamide include coconut oil fatty acid monoethanolamide, lauric acid monoethanolamide, palmitic acid monoethanolamide, stearic acid monoethanolamide, and the like.

The fatty acid monoalkylolamide is formulated in an amount of preferably 3% by weight or more and more preferably 5% by weight or more, of the raw materials for pearly luster, from the viewpoint of exhibiting a sufficient pearly luster, and in an amount of preferably 15% by weight or less and more preferably 10% by weight or less, of the raw materials for pearly luster, from the viewpoint of suppressing an increase in the viscosity of the pearly luster composition and increasing fluidity. From the above viewpoints, the fatty acid monoalkylolamide is formulated in an amount of preferably from 3 to 15% by weight, more preferably from 3 to 10% by weight, and even more preferably from 5 to 10% by weight, of the raw materials for pearly luster.

Further, as the raw materials for pearly luster, besides the above-mentioned components, for example, a pH adjusting agent, a preservative, a viscosity reducing agent, a crystallizing agent, salts, alcohols, polyols or the like, may be appropriately used in a proper amount.

Incidentally, the balance of the raw materials for pearly luster is water. The water is formulated in an amount of preferably from 25 to 75% by weight, more preferably from 40 to 75% by weight, and even more preferably from 50 to 75% by weight, of the raw materials for pearly luster, from the viewpoint of giving an appropriate viscosity to the pearly luster composition.

In the present invention, the pearly luster composition is obtained using the fatty acid glycol ester (a1), the fatty acid glycol ester (a2), the surfactant and the like, described above, by a method including the following steps (i) to (iii).

The step (i) is a step of solubilizing the fatty acid glycol ester (a2) in the presence of the surfactant (B). Here, the term "solubilizing" refers to a process of dissolving the fatty acid glycol ester (a2), which is an oily substance, in a micelle formed by the surfactant. While a part of droplets of the fatty acid glycol ester (a2) may be present in a solubilized solution, it is not preferable that the fatty acid glycol ester (a2) is precipitated as a crystal.

In the step (i), for example, a solid fatty acid glycol ester (a2) may be added to an aqueous solution of the surfactant, and the mixture may be heated until the fatty acid glycol ester (a2) is solubilized. Also, a molten fatty acid glycol ester (a2) may be added to an aqueous solution of the surfactant heated to a temperature at which the fatty acid glycol ester (a2) is not crystallized even if the molten fatty acid glycol ester (a2) is added thereto.

It is preferable that the raw materials for pearly luster besides the fatty acid glycol ester (a1) are previously formulated in the solution to which the fatty acid glycol ester (a2) is added in the step (i).

The subsequent step (ii) is a step of mixing the solubilized solution obtained in the step (i) with a molten fatty acid glycol ester (a1), to emulsify the mixture.

It is preferable that the fatty acid glycol ester (a1) to be mixed in the step (ii) is mixed in an amount such that the fatty acid glycol ester (a1) mixed forms droplets. Here, the formation of droplets is realized by a mixture in an amount exceeding the amount solubilized. Specifically, the formation of droplets is confirmed in a mixture in an amount of 0.5% by weight or more of the pearly luster composition. The formation of droplets can be confirmed by a visual observation due to the generation of turbidity, or lowering of a visible light or ultraviolet transmittance.

As the pearly luster particles (A) contained in the pearly luster composition obtained by the method of the present invention, those having a structure mainly containing large amounts of the fatty acid glycol ester (a1) in the central part and the fatty acid glycol ester (a2) in the surface part are preferable. In order to realize the above structure, it is preferable that the fatty acid glycol ester (a2) is present in the system in a solubilized state, and the fatty acid glycol ester (a1) forms droplets in the system. By realizing the structure, it is presumed that the fatty acid glycol ester (a1) is first crystallized to form seed crystals, and the fatty acid glycol ester (a2) is precipitated on a surface thereof.

In other words, it is preferable that the mixing of the solubilized solution obtained in the step (i) and the fatty acid glycol ester (a1) is carried out before crystals of the fatty acid glycol ester (a2) are precipitated.

Therefore, a method of mixing the solubilized solution obtained in the step (i) and the molten fatty acid glycol ester (a1) is not specifically limited, and an embodiment including the step of adding a molten fatty acid glycol ester (a1) to the solubilized solution obtained in the step (i) is preferable, from the viewpoint of forming droplets of the fatty acid glycol ester (a1) in the system.

The fatty acid glycol ester (a1) is mixed in a molten state, and it is preferable that the fatty acid glycol ester (a1) is mixed to form droplets while the molten state is maintained, preferably at a temperature equal to or higher than the melting point of the fatty acid glycol ester (a1), from the above viewpoint. The temperature of the solubilized solution obtained in the step (i), upon mixing with the molten fatty acid glycol ester (a1), is equal to or higher than preferably a temperature calculated from the melting point of the fatty acid glycol ester (a1)−(minus) 10° C., and more preferably a temperature calculated from the melting point−(minus) 5° C.

In addition, the solubilized fatty acid glycol ester (a2) is incorporated with the passage of time into the fatty acid glycol ester (a1) forming droplets. Then, the amount of the fatty acid glycol ester (a2) in the surface part of the pearly luster particles (A) is reduced. Therefore, since it is preferable to shorten the time period for incorporating the solubilized fatty acid glycol ester (a2) into the fatty acid glycol ester (a1) forming droplets, the mixing with the fatty acid glycol ester (a1) is preferably carried out at a lower temperature, and at a temperature equal to or lower than preferably a temperature calculated from the melting point of the fatty acid glycol ester (a1) +(plus) 20° C., and more preferably a temperature calculated from the melting point +(plus) 10° C.

From the above viewpoint, the temperature of the solubilized solution to be mixed with the molten fatty acid glycol ester (a1) is preferably equal to or higher than a temperature calculated from the melting point of the fatty acid glycol ester (a1) −(minus) 10° C. and equal to or lower than a temperature calculated from the melting point +(plus) 20° C., and more preferably equal to or higher than a temperature calculated from the melting point −(minus) 5° C. and equal to or lower than a temperature calculated from the melting point +(plus) 10° C.

The step (iii) is a step of cooling the emulsified mixture obtained in the step (ii), to precipitate the pearly luster particles (A). When a temperature distribution occurs in the raw materials for pearly luster during cooling, a distribution of shapes of the resulting pearly luster particles (A) is also generated. Therefore, in order to obtain pearly luster particles (A) with uniform shapes, a gradual cooling with a small temperature distribution is preferable. The cooling rate is preferably from 0.1° to 10° C./min, more preferably from 0.1° to 5° C./min, and even more preferably from 0.1° to 3° C./min. Also, it is desired that the cooling is carried out until the temperature of the emulsified mixture is preferably from 10° to 40° C., and more preferably from 15° to 35° C.

In the present invention, the time period from the mixing of the fatty acid glycol ester (a1) in the step (ii) up to the precipitation of the pearly luster particles (A) in the step (iii) is preferably within 120 minutes, and more preferably within 100 minutes, from the viewpoint of shortening the time period for incorporating the solubilized fatty acid glycol ester (a2) into the fatty acid glycol ester (a1) that forms droplets. The lower limit of the time period is not specifically limited, but is preferably 5 minutes or more, from the viewpoint of cooling capability.

The pearly luster particles (A) is usually obtained in the shape of a plate-like crystal having a major axis length of from 2 to 100 μm, a minor axis length of from 0.5 to 50 μm and a thickness of from 0.05 to 2 μm. The shape and size of the crystals can be properly adjusted according to its applications or the like, by the kinds, combination, and the amount of the surfactant, and further by the cooling rate, the stirring intensity, and the like.

The pearly luster particles obtained by the method of the present invention have properties that are not only excellent in luster, but also stable even at a high temperature. When the pearly luster particles have a structure containing large amounts of each of the fatty acid glycol ester (a1) in the central part and the fatty acid glycol ester (a2) in the surface part, the pearly luster particles have a higher resistance also to hydrolysis under high-temperature environmental conditions. Therefore, the pearly luster particles of the present invention are formulated in shampoos, rinses, body shampoos, liquid detergents, and the like, and whereby the added values thereof can be even more enhanced.

Therefore, in the present invention, as a more preferred embodiment using the pearly luster composition obtained by the method of the present invention, a shampoo containing the pearly luster composition is provided.

The content of the pearly luster composition in the shampoo is not particularly limited, and the pearly luster composition is contained in an amount of preferably from 1 to 30% by weight, and more preferably from 2 to 20% by weight.

The shampoo of the present invention can be produced in the same manner as in the ordinary shampoo using a known additive such as a surfactant, water, or the like, according to its purposes or the like, except that the pearly luster composition obtained by the present invention is used. The timing of adding and the method of adding the pearly luster composition are also not particularly limited, as long as the pearly luster obtained by the pearly luster composition is not impaired.

EXAMPLES

The following examples further describe and demonstrate embodiments of the present invention. The examples are given solely for the purposes of illustration and are not to be construed as limitations of the present invention.

The properties of the pearly luster compositions obtained in each of Examples and each of Comparative Examples, were determined according to the following methods.

<Appearance of Pearly Luster Composition and Shape of Crystals>

(1) Evaluation Criteria of Appearance of Pearly Luster Composition

Ion-exchanged water is added to the pearly luster composition, so that the concentration of the pearly luster composition is 2% by weight, and the mixture is stirred, to have a homogenous composition. Thereafter, the appearance of a dilution of the resulting pearly luster composition is visually observed, and evaluated according to the following evaluation criteria.

[Evaluation Criteria]
4: The pearly luster composition has a very high luster.
3: The pearly luster composition has a high luster.
2: The pearly luster composition has a weak luster.
1: The pearly luster composition has a slight luster (like an emulsion).

(2) Shapes of Crystals

A microphotograph of the dilution is taken with a color laser microscope, and major axis lengths, minor axis lengths and thicknesses of the 30 crystals are determined, and each median value is defined as a representative value of the crystal shapes.

<Method for Determining Hydrolysis Rate>

(a) Preparation of Internal Standard Solution

The amount 0.1 g of 1,4-dinitrobenzene is dissolved in 100 ml of deuterated chloroform, to prepare an internal standard solution.

(b) Storage

The pearly luster composition is dispersed in the shampoo having a composition shown in Table 1 so as to have a concentration of 10% by weight, and the dispersion is divided in two. One is stored at 5° C. for 1 month, and the other is stored at 50° C. for 1 month.

TABLE 1

| Composition | % by wt. |
|---|---|
| Ammonium Laureth Sulfate (Effective Content of 70%) | 10.00 |
| Lauramidepropyl Betaine | 1.00 |
| Cocamide MEA | 0.50 |
| Laureth-16 | 0.50 |
| Polyoctanium-10 | 0.50 |
| Guar-Hydroxypropyltrimonium Chloride | 0.50 |
| Cetearyl Alcohol | 0.50 |
| Myristyl Alcohol | 0.50 |
| Dimethicone Emulsion | 2.00 |
| Pearly Luster Composition | 10.00 |
| Malic Acid (Effective Content of 50%) | 0.40 |
| Lactic Acid (Effective Content of 50%) | 0.38 |
| Benzyl Alcohol | 0.50 |
| Perfume | 0.50 |
| PPG-9 | Viscosity Adjustment |
| Citric Acid | pH Adjustment |
| Water | Balance |
| pH | 3.7 |
| Viscosity | 6000 mPa·s |

(c) Preparation of Sample Solution

The amount 0.05 g of the shampoo stored at 5° C. for 1 month is dried under reduced pressure at ambient temperature for 3 days. Deuterated water is added thereto to disperse, and the mixture is again dried under reduced pressure in the same manner as the above. This procedure is repeated once more to obtain a dried solid product. Two milliliters of the internal standard solution and 1 ml of deuterated methanol are added to the dried solid product, to dissolve the dried solid product. The shampoo stored at 50° C. for 1 month is similarly made as a solidified product, and dissolved with the internal standard solution and deuterated methanol.

(d) NMR (Nuclear Magnetic Resonance Analysis) Determination

Each of the sample solutions stored at 5° C. and stored at 50° C. prepared in item (c) is determined with NMR (Mercury 400) under the determination conditions of a determination mode of Proton 1D, a solvent of CD3OD, the determination temperature at room temperature, and the cumulative number of 8 times.

(e) Calculation of Hydrolysis Rate

An integral value of a signal of δ=8.4 ppm of 1,4-dinitrobenzene and an integral value of a signal at δ=4.25 ppm of a fatty acid ethylene glycol are quantitated for both of the sample solutions stored at 5° C. and stored at 50° C., and the hydrolysis rate is calculated according to the following equation.

$$\text{Hydrolysis Rate (\%)} = 100 - \frac{\begin{array}{c}\text{Integral Value (4.25 ppm) of}\\\text{Fatty Acid Ethylene Glycol}\\\text{of Sample Solution Prepared}\\\text{from Shampoo Stored at 50° C.}\\\hline\text{Integral Value (8.4 ppm) of}\\\text{1, 4-Dinitrobenzene of Sample}\\\text{Solution Prepared from}\\\text{Shampoo Stored at 50° C.}\end{array}}{\begin{array}{c}\text{Integral Value (4.25 ppm) of}\\\text{Fatty Acid Ethylene Glycol}\\\text{of Sample Solution Prepared}\\\text{from Shampoo Stored at 5° C.}\\\hline\text{Integral Value (8.4 ppm) of}\\\text{1, 4-Dinitrobenzene of Sample}\\\text{Solution Prepared from}\\\text{Shampoo Stored at 5° C.}\end{array}} \times 100 \quad [\text{Math 1}]$$

<Method for Determining Melting Point>

The fatty acid ethylene glycol is heated so as to raise the temperature at a rate of 5° C./min using a differential scanning calorimeter (Thermo plus DSC8230, manufactured by Rigaku Corporation), and the top of the resulting melting peak is defined as a melting point.

Example 1

[Step (i)]

A 300-mL separable flask was charged with 120.75 g of raw materials from the raw materials for pearly luster shown in Table 2 excluding a fatty acid ethylene glycol (a1). Here, a fatty acid ethylene glycol (a2) is a di-fatty acid ethylene glycol, wherein $A^2$ is an ethylene group and y is 1 in the formula (II), which is mainly composed of ethylene glycol distearate, of which fatty acid moiety is constituted by 98% by weight of stearic acid, 1% by weight of palmitic acid, and 1% by weight of the other fatty acids, and the fatty acid ethylene glycol had a melting point of 74.5° C. These raw materials were heated to a temperature of 85° C., and thereafter stirred at a rate of 100 r/min at 85° C. for 10 minutes, to give a solubilized solution of the fatty acid ethylene glycol (a2).

TABLE 2

| Raw Materials for Pearly Luster | Amount Formulated | |
|---|---|---|
| | g | % by wt. |
| Fatty Acid Ethylene Glycol (a2) | 0.75 | 0.5 |
| Fatty Acid Ethylene Glycol (a1) | 29.25 | 19.5 |
| Sodium Polyoxyethylene(2EO) Lauryl Ether Sulfate | 16.20 | 10.8 |
| Polyoxyethylene(4EO) Lauryl Ether (HLB = 9.7) | 6.00 | 4.0 |
| Coconut Oil Fatty Acid Monoethanolamide | 11.25 | 7.5 |
| Water | 85.35 | 56.9 |
| Citric Acid | 0.15 | 0.1 |
| Sodium Benzoate | 1.05 | 0.7 |
| Total Amount | 150.00 | 100.0 |

Note)
The number that precedes EO shows the number of moles of ethylene oxide.

[Step (ii)]

The solubilized solution in the separable flask was cooled at a rate of 0.5° C./min while stirring. When the temperature of the solution was 60° C., 19.5% by weight (29.25 g) of the fatty acid ethylene glycol (a1) molten at 80° C. was added thereto. Here, the fatty acid ethylene glycol (a1) is a di-fatty acid ethylene glycol, wherein $A^1$ is an ethylene group and x is 1 in the formula (I), which is a mixture of ethylene glycol dipalmitate, ethylene glycol monopalmitate and monostearate, and ethylene glycol distearate, of which fatty acid moiety is constituted by 50% by weight of palmitic acid, 49% by weight of stearic acid, and 1% by weight of the other fatty acids, and the fatty acid ethylene glycol had a melting point of 61.6° C.

[Step (iii)]

Further, the mixture was cooled at a rate of 0.17° C./min for 47 minutes, and crystals were then precipitated. The cooling was terminated when the temperature reached 35° C., thereby giving a pearly luster composition. The appearance and the hydrolysis rate of the resulting pearly luster composition are shown in Table 3.

Example 2

The same procedures as in Example 1 were carried out except that the temperature upon adding the molten fatty acid ethylene glycol (a1) in Example 1 was changed to 65° C., to give a pearly luster composition. The appearance and the hydrolysis rate of the resulting pearly luster composition are shown in Table 3.

Comparative Example 1

The step (i) was carried out in the same manner as in Example 1, to give the solubilized solution at 85° C. This solution was cooled to 55° C. at a rate of 0.5° C./min while stirring, to crystallize a fatty acid ethylene glycol (a2). Thereto was added 19.5% by weight (29.25 g) of a molten fatty acid ethylene glycol (a1), and the mixture was further cooled, to give a pearly luster composition. The appearance and the hydrolysis rate of the resulting pearly luster composition are shown in Table 3.

Example 3

The same procedures as in Example 2 were carried out except that, in the raw materials for pearly luster in Example 2, the amount of the fatty acid ethylene glycol (a2) formulated was changed to 1.0% by weight (1.5 g) and the amount of the fatty acid ethylene glycol (a1) formulated was changed to 19.0% by weight (28.5 g), to give a pearly luster composition. In other words, the temperature of the molten fatty acid ethylene glycol (a1) upon addition was 65° C. The appearance and the hydrolysis rate of the resulting pearly luster composition are shown in Table 4. In addition, the resulting pearly luster composition had a shape having a major axis length of 3.98 μm, a minor axis length of 2.89 μm, and a thickness of 0.37 μm, and had a very high luster.

Example 4

The same procedures as in Example 3 were carried out except that the temperature upon addition of the molten fatty acid ethylene glycol (a1) in Example 3 was changed to 80° C., to give a pearly luster composition. The appearance and the hydrolysis rate of the resulting pearly luster composition are shown in Table 4.

Comparative Example 2

The same procedures as in Example 3 were carried out except that, in the step (i) of Example 3, a separable flask was charged with raw materials excluding the fatty acid ethylene glycol (a1) and the fatty acid ethylene glycol (a2) from the raw materials for pearly luster, the raw materials in the flask were heated to a temperature of 85° C., thereafter the molten mixture of the fatty acid ethylene glycol (a1) and the fatty acid ethylene glycol (a2) were added thereto, the mixture was stirred at a rate of 100 r/min at 85° C. for 10 minutes, and the resulting emulsified mixture was subjected to the step (iii), to give a pearly luster composition. The appearance and the hydrolysis rate of the resulting pearly luster composition are shown in Table 4.

Comparative Example 3

The solubilized solution at 85° C. was prepared in the same manner as in Example 3, and the solution was cooled to 60° C., to crystallize a fatty acid ethylene glycol (a2). Thereto was added a molten fatty acid ethylene glycol (a1), and the mixture was further cooled, to give a pearly luster composition. The appearance and the hydrolysis rate of the resulting pearly luster composition are shown in Table 4.

Example 5

The same procedures as in Example 2 were carried out except that, in the raw materials for pearly luster in Example 2, the amount of the fatty acid ethylene glycol (a2) formulated was changed to 3.0% by weight (4.5 g) and the amount of the fatty acid ethylene glycol (a1) formulated was changed to 17.0% by weight (25.5 g), to give a pearly luster composition. In other words, the temperature of the molten fatty acid ethylene glycol (a1) upon addition was 65° C. The appearance and the hydrolysis rate of the resulting pearly luster composition are shown in Table 5.

Example 6

The same procedures as in Example 5 were carried out except that the temperature upon addition of the molten fatty acid ethylene glycol (a1) in Example 5 was changed to 80° C., to give a pearly luster composition. The appearance and the hydrolysis rate of the resulting pearly luster composition are shown in Table 5.

Comparative Example 4

The same procedures as in Example 5 were carried out except that, in the step (i) of Example 5, a separable flask was charged with raw materials excluding the fatty acid ethylene glycol (a1) and the fatty acid ethylene glycol (a2) from the raw materials for pearly luster, the raw materials in the flask were heated to a temperature of 85° C., thereafter the molten mixture of the fatty acid ethylene glycol (a1) and the fatty acid ethylene glycol (a2) were added thereto, the mixture was stirred at a rate of 100 r/min at 85° C. for 10 minutes, and the resulting emulsified mixture was subjected to the step (iii), to give a pearly luster composition. The appearance and the hydrolysis rate of the resulting pearly luster composition are shown in Table 5.

Example 7

The same procedures as in Example 2 were carried out except that, in the raw materials for pearly luster in Example 2, the amount of the fatty acid ethylene glycol (a2) formulated was changed to 4.0% by weight (6.0 g) and the amount of the fatty acid ethylene glycol (a1) formulated was changed to 16.0% by weight (24.0 g), to give a pearly luster composition. In other words, the temperature of the molten fatty acid ethylene glycol (a1) upon addition was 65° C. The appearance and the hydrolysis rate of the resulting pearly luster composition are shown in Table 6. In addition, the resulting pearly luster composition had a shape having a major axis length of 3.61 μm, a minor axis length of 2.57 μm, and a thickness of 0.64 μm, and had a very high luster.

Comparative Example 5

The same procedures as in Example 7 were carried out except that, in the step (i) of Example 7, a separable flask was charged with raw materials excluding the fatty acid ethylene glycol (a1) and the fatty acid ethylene glycol (a2) from the raw materials for pearly luster, the raw materials in the flask were heated to a temperature of 85° C., thereafter the molten mixture of the fatty acid ethylene glycol (a1) and the fatty acid ethylene glycol (a2) were added thereto, the mixture was stirred at a rate of 100 r/min at 85° C. for 10 minutes, and the resulting emulsified mixture was subjected to the step (iii), to give a pearly luster composition. The appearance and the hydrolysis rate of the resulting pearly luster composition are shown in Table 6.

Comparative Example 6

The same procedures as in Example 1 were carried out in that, in the step (i), a separable flask was charged with raw materials without formulating a fatty acid ethylene glycol (a2), and the amount of a fatty acid ethylene glycol (a1) formulated was changed to 20.0% by weight (30.0 g) in the raw materials for pearly luster shown in Table 2, the raw materials were emulsified at 80° C., and the emulsified mixture was subjected to the step (iii), to give a pearly luster composition. The appearance and the hydrolysis rate of the resulting pearly luster composition are shown in

TABLE 3

|  | Comp. Ex. 1 | Ex. 1 | Ex. 2 |
| --- | --- | --- | --- |
| Fatty Acid Ethylene Glycol (a2) | 0.5% by wt. | 0.5% by wt. | 0.5% by wt. |
| Fatty Acid Ethylene Glycol (a1) | 19.5% by wt. | 19.5% by wt. | 19.5% by wt. |
| Method of Adding (a1) | After (a2) Precipitation, Addition at 55° C. | Before (a2) Precipitation, Addition at 60° C. | Before (a2) Precipitation, Addition at 65° C. |
| Time Period from Addition of (a1) up to Precipitation of Crystal (Minutes) | — | 47 | 58 |
| Appearance | 4 | 4 | 4 |
| Hydrolysis Rate (%) | 33.2 | 23.0 | 20.3 |

TABLE 4

|  | Comp. Ex. 2 | Comp. Ex. 3 | Ex. 3 | Ex. 4 |
| --- | --- | --- | --- | --- |
| Fatty Acid Ethylene Glycol (a2) | 1.0% by wt. | 1.0% by wt. | 1.0% by wt. | 1.0% by wt. |
| Fatty Acid Ethylene Glycol (a1) | 19.0% by wt. | 19.0% by wt. | 19.0% by wt. | 19.0% by wt. |
| Method of Adding (a1) | Melting (a1) and (a2) and Mixing | After (a2) Precipitation, Addition at 60° C. | Before (a2) Precipitation, Addition at 65° C. | Before (a2) Precipitation, Addition at 80° C. |
| Time Period from Addition of (a1) up to Precipitation of Crystal (Minutes) | — | — | 55 | 83 |
| Appearance | 4 | 4 | 4 | 4 |
| Hydrolysis Rate (%) | 29.5 | 30.2 | 19.4 | 25.6 |

TABLE 5

|  | Comp. Ex. 4 | Ex. 5 | Ex. 6 |
| --- | --- | --- | --- |
| Fatty Acid Ethylene Glycol (a2) | 3.0% by wt. | 3.0% by wt. | 3.0% by wt. |
| Fatty Acid Ethylene Glycol (a1) | 17.0% by wt. | 17.0% by wt. | 17.0% by wt. |
| Method of Adding (a1) | Melting (a1) and (a2) and Mixing | Before (a2) Precipitation, Addition at 65° C. | Before (a2) Precipitation, Addition at 80° C. |
| Time Period from Addition of (a1) up to Precipitation of Crystal (Minutes) | — | 49 | 83 |
| Appearance | 4 | 4 | 4 |
| Hydrolysis Rate (%) | 28.9 | 21.6 | 22.8 |

TABLE 6

|  | Comp. Ex. 5 | Ex. 7 | Comp. Ex. 6 |
| --- | --- | --- | --- |
| Fatty Acid Ethylene Glycol (a2) | 4.0% by wt. | 4.0% by wt. | 0% by wt. |
| Fatty Acid Ethylene Glycol (a1) | 16.0% by wt. | 16.0% by wt. | 20.0% by wt. |
| Method of Adding (a1) | Melting (a1) and (a2) and Mixing | Before (a2) Precipitation, Addition at 65° C. | Addition at 80° C. |
| Time Period from Addition of (a1) up to Precipitation of Crystal (Minutes) | — | 51 | — |
| Appearance | 4 | 4 | 4 |
| Hydrolysis Rate (%) | 32.0 | 22.0 | 31.9 |

It can be seen from the above results that the pearly luster compositions obtained in Examples are not only excellent in luster, but also are stable with a low hydrolysis rate even in storage at a high temperature, as compared to those obtained in Comparative Examples.

The pearly luster composition obtained by the present invention is suitably used for shampoos, rinses, body shampoos, liquid detergents, and the like.

The invention claimed is:

1. A method for producing a pearly luster composition comprising pearly luster particles (A) comprising a fatty acid glycol ester (a1) represented by the formula (I):

$$R^1COO\text{-}(A^1O)_x\text{—}COR^2 \qquad (I)$$

wherein each of $R^1$ and $R^2$ is independently an alkyl group having 13 to 21 carbon atoms, $A^1$ is a —$C_2H_4$— group or a —$C_3H_6$— group, and x is the number of from 1 to 10, and a fatty acid glycol ester (a2) represented by the formula (II):

$$R^3COO\text{-}(A^2O)_y\text{—}COR^4 \qquad (II)$$

wherein each of $R^3$ and $R^4$ is independently an alkyl group having 15 to 21 carbon atoms, $A^2$ is a —$C_2H_4$— group or a —$C_3H_6$— group, and y is the number of from 1 to 10, wherein said fatty acid glycol ester (a2) has a melting point higher than the melting point of the fatty acid glycol ester (a1), and a surfactant (B), wherein the method comprises the steps of;
(i) solubilizing the fatty acid glycol ester (a2) in the presence of the surfactant (B);
(ii) mixing the solubilized solution obtained in the step (i) with a molten fatty acid glycol ester (a1), to emulsify the mixture, such that said mixing is before precipitation of crystals of said fatty acid glycol ester (a2); and
(iii) cooling the emulsified mixture obtained in the step (ii), to precipitate the pearly luster particles (A).

2. The method according to claim 1, wherein the temperature of the solubilized solution to be mixed with the molten fatty acid glycol ester (a1) in the step (ii) is equal to or higher than a temperature calculated from the melting point of the fatty acid glycol ester (a1) −(minus) 10° C. and equal to or lower than a temperature calculated from the melting point +(plus) 20° C.

3. The method according to claim 1, wherein the fatty acid glycol ester (a1) is mixed in the step (ii) in an amount such that the fatty acid glycol ester (a1) forms droplets.

4. The method according to claim 1, wherein the time period from the mixture of the fatty acid glycol ester (a1) in the step (ii) up to the precipitation of the pearly luster particles (A) in the step (iii) is 120 minutes or less.

5. A pearly luster composition obtained by the method as defined in claim 1.

6. A shampoo comprising the pearly luster composition as defined in claim 5.

7. The method according to claim 2, wherein the fatty acid glycol ester (a1) is mixed in the step (ii) in an amount such that the fatty acid glycol ester (a1) forms droplets.

8. The method according to claim 1, wherein the fatty acid glycol ester (a1) is crystalline and has a melting point of 50° C. or higher,
the fatty acid glycol ester (a2) is crystalline and has a melting point of 60° C. or higher, and
the fatty acid glycol ester (a2) has a melting point higher than the melting point of the fatty acid glycol ester (a1) by 5° C. to 20° C.

9. The method according to claim 1, the fatty acid glycol ester (a1) is formulated in an amount from 15 to 30% by weight of the pearly luster composition.

10. The method according to claim 1, the fatty acid glycol ester (a2) is formulated in an amount of $1/100$ to $50/100$ of the amount of the fatty acid glycol ester (a1).

11. The method according to claim 1, the surfactant (B) comprises an anionic surfactant.

12. The method according to claim 1, the anionic surfactant is formulated in an amount of from 5 to 15% by weight of the pearly luster composition.

13. The method according to claim 1, the surfactant (B) comprises a nonionic surfactant.

14. The method according to claim 1, the nonionic surfactant is formulated in an amount of 0.5 to 10% by weight of the pearly luster composition.

15. The method according to claim 1, the pearly luster composition comprises a fatty acid monoalkylolamide.

16. The method according to claim 15, the fatty acid monoalkylolamide is formulated in an amount of from 3 to 15% by weight of the pearly luster composition.

\* \* \* \* \*